United States Patent [19]
Wildman

[11] Patent Number: 5,863,199
[45] Date of Patent: *Jan. 26, 1999

[54] LINGUAL BRACKET WITH HINGED CAMMING CLOSURE AND LOCKING EARS

[76] Inventor: Alexander J. Wildman, 2662 Donner Pla., Eugene, Oreg. 97401

[*] Notice: The term of this patent shall not extend beyond the expiration date of Pat. No. 5,700,145.

[21] Appl. No.: 984,122

[22] Filed: Dec. 3, 1997

Related U.S. Application Data

[63] Continuation of PCT/US96/05959, Apr. 29, 1996 which is a continuation-in-part of Ser. No. 602,577, Feb. 16, 1996, Pat. No. 5,700,145, which is a continuation-in-part of Ser. No. 473,117, Jun. 5, 1995, Pat. No. 5,511,976.

[51] Int. Cl.$^6$ .................................................. A61C 7/100
[52] U.S. Cl. ................................................ 433/10; 433/11
[58] Field of Search ................................... 433/8, 10, 11, 433/12, 13

[56] References Cited

U.S. PATENT DOCUMENTS

| | | |
|---|---|---|
| 678,453 | 7/1901 | Angle . |
| 1,552,413 | 8/1925 | Angle . |
| 1,584,501 | 5/1926 | Angle . |
| 1,821,171 | 9/1931 | Atkinson . |
| 1,949,444 | 3/1934 | Angle . |
| 1,952,320 | 3/1934 | Johnson . |
| 2,023,849 | 12/1935 | McCoy . |
| 2,196,516 | 4/1940 | Atkinson . |
| 2,305,916 | 12/1942 | Atkinson . |
| 2,406,527 | 8/1946 | Berke . |
| 2,665,480 | 1/1954 | Johnson . |
| 2,705,367 | 4/1955 | Berke . |
| 2,756,502 | 7/1956 | Bowles . |
| 2,759,265 | 8/1956 | Johnson . |
| 2,854,747 | 10/1958 | Lewis . |
| 3,091,857 | 6/1963 | Rubin et al. .............................. 433/11 |
| 3,128,553 | 4/1964 | Begg . |
| 3,302,288 | 2/1967 | Tepper . |
| 3,477,128 | 11/1969 | Andrews . |
| 3,593,421 | 7/1971 | Brader . |
| 3,660,900 | 5/1972 | Andrews . |
| 3,748,740 | 7/1973 | Wildman . |
| 3,775,850 | 12/1973 | Northcutt . |
| 3,780,437 | 12/1973 | Wildman . |
| 3,842,503 | 10/1974 | Wildman . |
| 3,854,207 | 12/1974 | Wildman . |
| 4,077,126 | 3/1978 | Pletcher . |
| 4,103,423 | 8/1978 | Kessel ....................................... 433/10 |
| 4,149,314 | 4/1979 | Nonnenmann ........................... 433/13 |
| 4,337,037 | 6/1982 | Kurz . |

(List continued on next page.)

OTHER PUBLICATIONS

ORMCO® Corporation, 1332 South Lone Hill Avenue, Glendora, California 91740, 1993 catalog, p. 27.

Wildman, Alexander J., "The Future of Lingual Orthodontics," *Orthodontics: Evaluation and Future,* Proceedings of the International Conference of the Orthodontic Dept. of Univ. of Nymegen, The Netherlands, Oct. 22–24, 1987, pp. 261–280 (1988).

*Primary Examiner*—Cary E. O'Connor
*Attorney, Agent, or Firm*—Marger Johnson & McCollon, P.C.

[57] ABSTRACT

A lingual orthodontic bracket includes a body (12) having a three-sided archwire slot (14, 414), and a hinged closure member (22, 422) pivotally and pivotable across the archwire slot and into a closed position in the closure member slot. The closure member includes a cam shaped central portion (28, 428A, 428B) extending across the archwire to retain it in the archwire slot under shear. The cam portion is convexly shaped to seat the archwire in the slot during closure. A bumper or rotation member (340, 440) can be used to bias the archwire against the closure member. The closure member (422) is formed with two sides that enclose the sides of the bracket and locking ears (425A, 425B) that engage the bracket body. The bracket includes two oppositely directed wings (418, 426) for receiving a ligature or O-ring.

26 Claims, 13 Drawing Sheets

U.S. PATENT DOCUMENTS

| | | |
|---|---|---|
| 4,386,908 | 6/1983 | Kurz . |
| 4,443,189 | 4/1984 | Wildman . |
| 4,492,573 | 1/1985 | Hanson . |
| 4,494,931 | 1/1985 | Wildman . |
| 4,551,094 | 11/1985 | Kesling . |
| 4,559,012 | 12/1985 | Pletcher ................................. 433/10 |
| 4,655,708 | 4/1987 | Fujita ................................. 433/10 |
| 4,698,017 | 10/1987 | Hanson ................................. 433/13 |
| 4,712,999 | 12/1987 | Rosenberg . |
| 4,713,001 | 12/1987 | Klein et al. . |
| 4,909,735 | 3/1990 | Wildman . |
| 5,011,406 | 4/1991 | Wildman . |
| 5,100,316 | 3/1992 | Wildman . |
| 5,224,858 | 7/1993 | Hanson . |
| 5,269,681 | 12/1993 | Degnan ................................. 433/11 |
| 5,295,886 | 3/1994 | Wildman . |
| 5,474,445 | 12/1995 | Voudouris ................................. 433/10 |
| 5,700,145 | 12/1997 | Wildman ................................. 433/11 |
| 5,738,513 | 4/1998 | Hermann ................................. 433/13 |

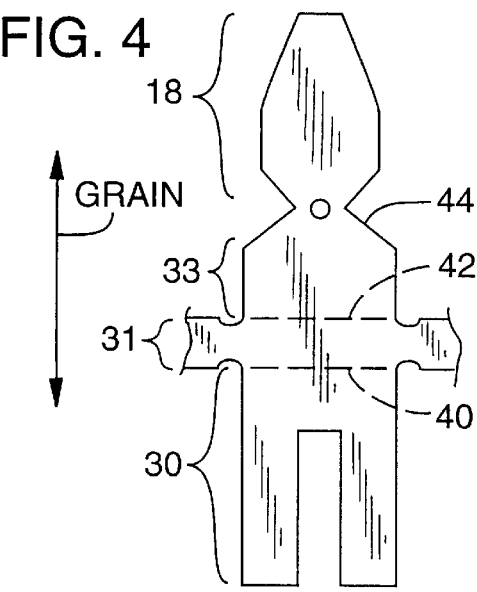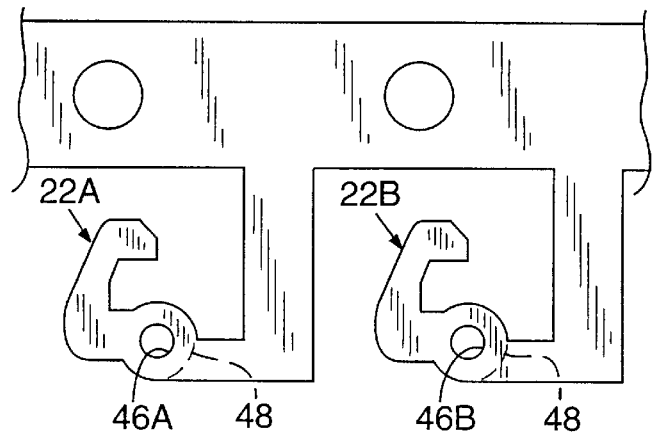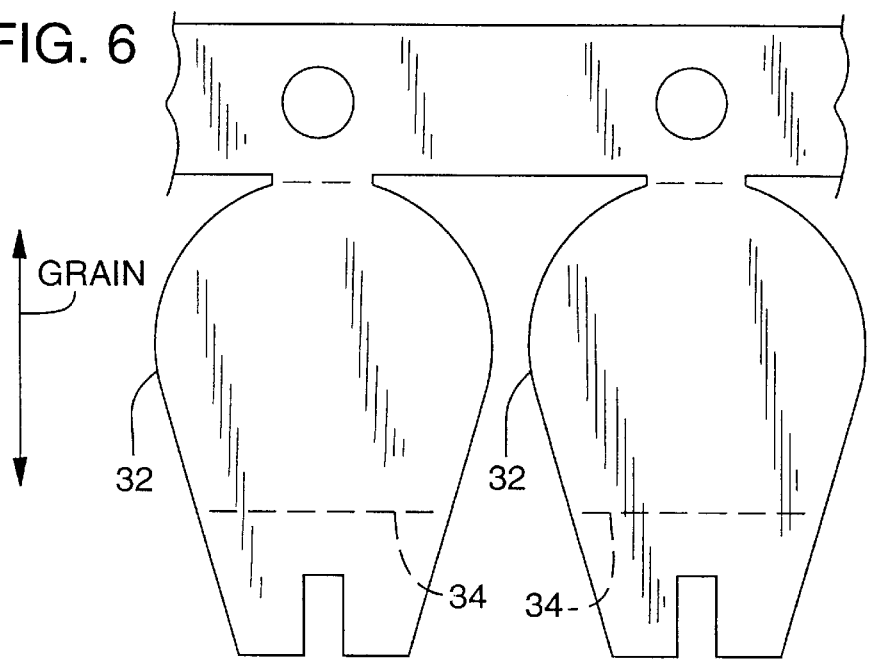

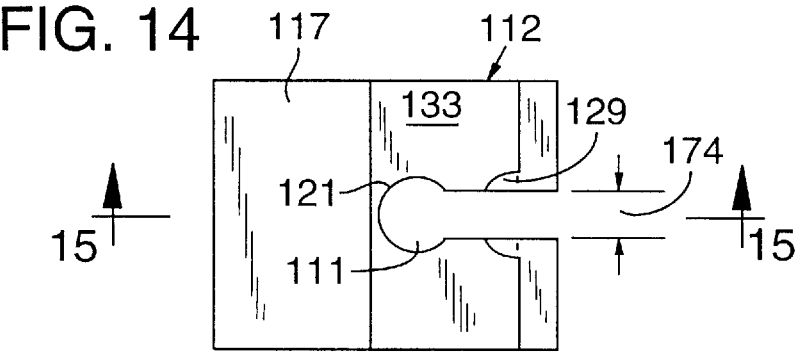
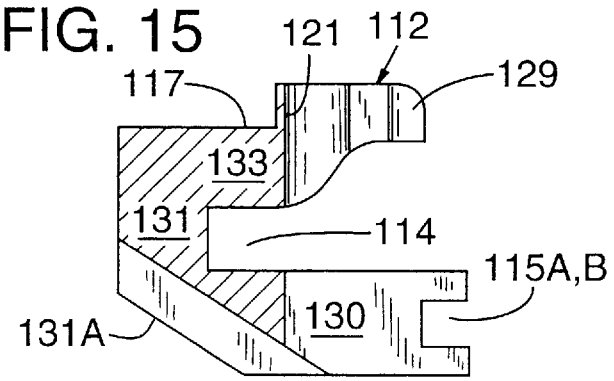
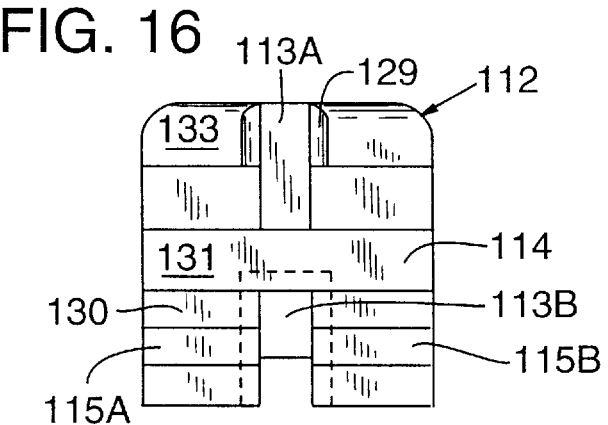

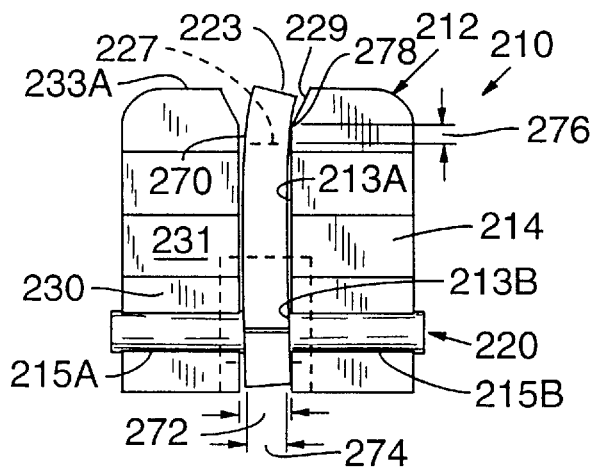
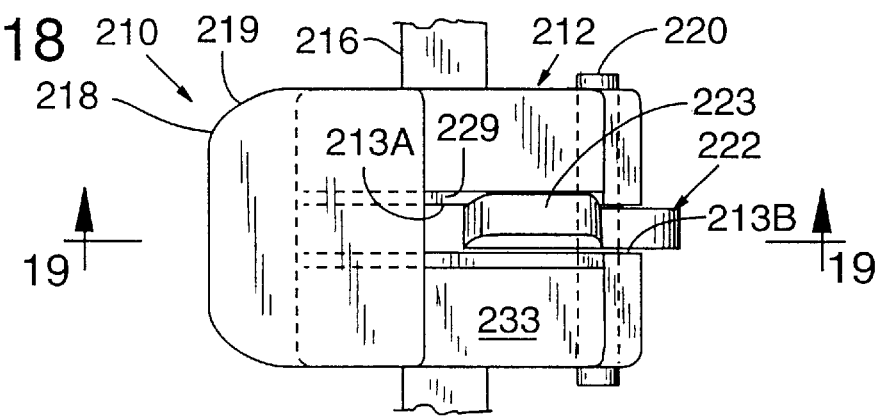
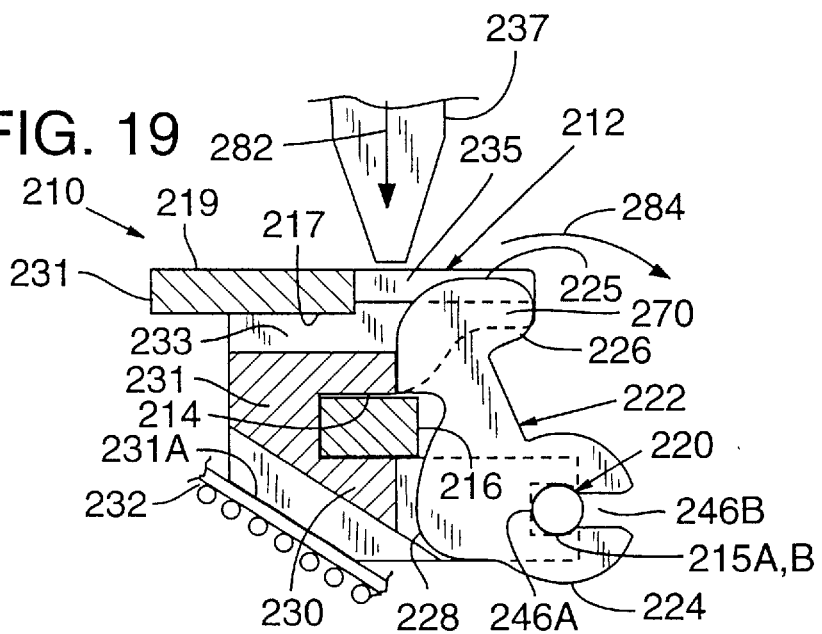

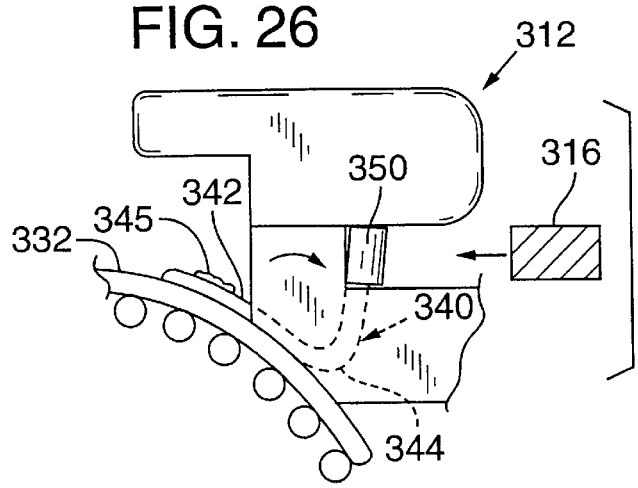
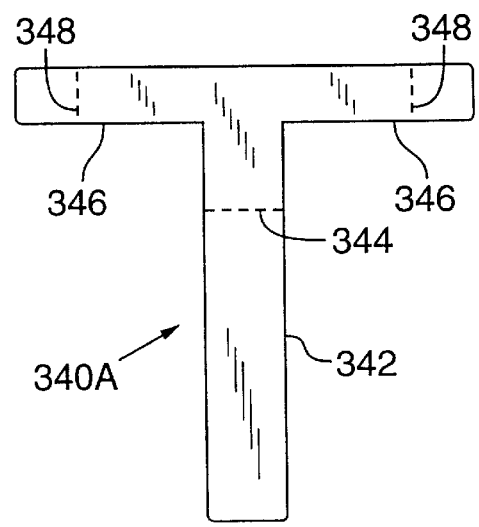
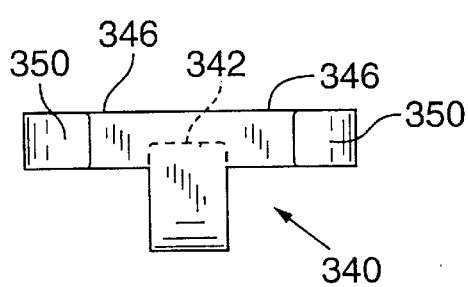
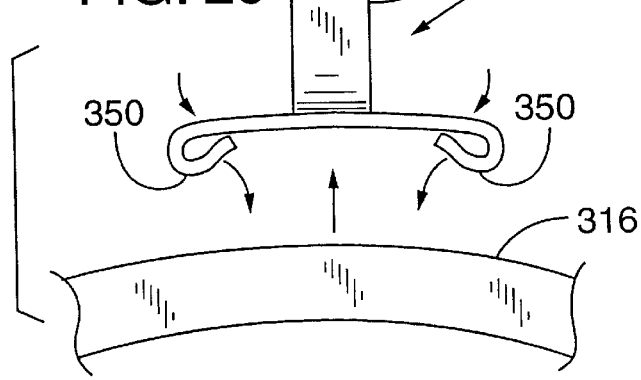

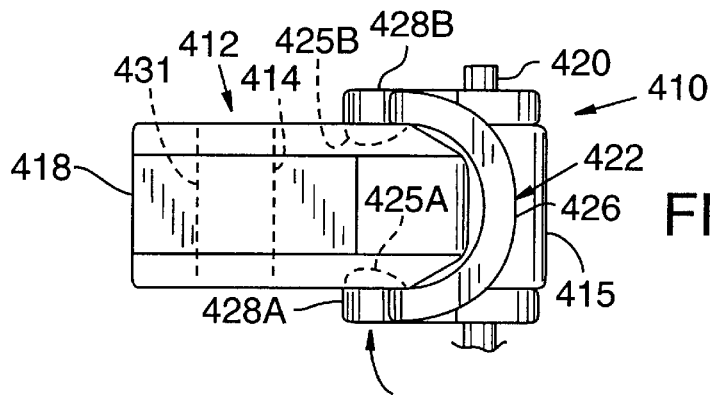
FIG. 31
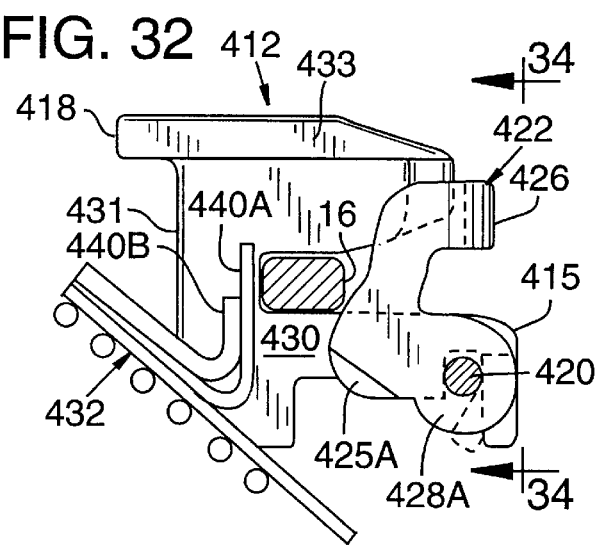
FIG. 32
FIG. 33
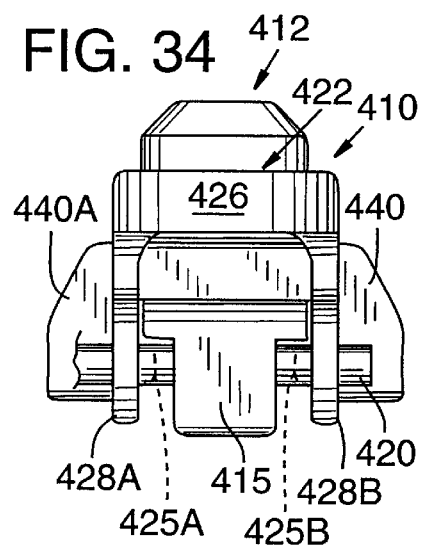
FIG. 34

# LINGUAL BRACKET WITH HINGED CAMMING CLOSURE AND LOCKING EARS

RELATED APPLICATION DATA

This application is a continuation-in-part of PCT application No. PCT/US96/05959, filed Apr. 29, 1996, entitled LINGUAL BRACKET WITH HINGED CAMMING CLOSURE AND RELEASABLE LOCK, designating the United States, and a CIP claiming priority from U.S. Ser. Nos. 08/602,577, filed Feb. 16, 1996, now U.S. Pat. No. 5,700,145, which is a CIP of 08/473,117, filed Jun. 5, 1995, now U.S. Pat. No. 5,511,976.

BACKGROUND OF THE INVENTION

This invention relates generally to orthodontic treatment and more particularly to a lingual orthodontic bracket and method of making same.

Orthodontic treatment of teeth is accomplished by applying force to the teeth with a spring-resilient archwire positioned in the channels in attachments on the teeth which are called brackets. Since the beginning of orthodontics in the late 1800's, orthodontists have been pursuing the goals of increased appliance resiliency and increased appliance control.

Edward H. Angle is considered the father of modern orthodontics. Angle's U.S. Pat. No. 678,453 shows a rigid outer archwire with teeth tied to the archwire to draw them into position (FIG. 1). The bands on the teeth were attachments which were really simple cleats. In 1925 in U.S. Pat. No. 1,584,501, Angle added a rectangular slot to the bracket with wings to receive tiewires (FIGS. 2 and 3). Because the slot was perpendicular to the long axis of the tooth, it was called the edgewise appliance. The initial heavy archwire was bent to the shape of the malocclusion and was gradually straightened out. This device produced very precise control but was extremely rigid and non-resilient.

Also in 1925, Angle was issued U.S. Pat. No. 1,552,413, which disclosed a bracket designed to receive a rectangular archwire that was called a ribbon arch because the long axis of the archwire cross section was in the same plane as the long axis of the tooth. This bracket was locked with a pin which was held in place by bending the pin after it was inserted in its locking position. This bracket was later used by Spencer Atkinson and was developed into what was known as the "Universal Technique" (FIG. 4). Atkinson's art was taught in U.S. Pat. Nos. 1,821,171; 2,196,516; and 2,305,916.

This same bracket was modified by Dr. P. R. Begg and was used extensively in what is called the "Begg Technique." Begg's modifications are described in U.S. Pat. No. 3,128,553. Dr. Angle's edgewise bracket has evolved into the "Edgewise Technique" which is the most commonly used technique today.

Typically, the archwire is secured in the archwire slot using an elastic O-ring or a wire ligature wrapped around wings extending laterally on opposite sides of the slot. An edgewise bracket can be augmented to provide traction hooks while assisting in securing the archwire in the archwire slot as disclosed in U.S. Pat. No. 4,713,001 to Klein. It is also known to use a retaining spring clip over the archwire slot in an edgewise bracket as disclosed in U.S. Pat. No. 4,551,094 to Kesling; U.S. Pat. No. 4,712,999 to Rosenberg; and the ORMCO Catalog, page 27 (1992). U.S. Pat. No. 4,492,573 to Hanson discloses a bracket which has an additional slot extending transversely under the archwire slot to slidably receive one leg of a spring clip while a second or external leg extends over one side of the bracket and has a distal end that protrudes into the archwire slot to hold the archwire.

To this evolution was incorporated the use of a number of archwires beginning with relatively small diameter round wires and finishing with the large rectangular edgewise wire. This progression of archwires provided a tremendous increase in resiliency. It also forced the orthodontist to go through a number of laborious archwire changes. To further increase the resiliency of the archwires, orthodontists incorporated all sorts of geometric bends in almost every conceivable shape (FIG. 5). These bends increased the resiliency but they decreased the amount of control. One example of lack of control is what is known as a closing loop. Closing loops are used to close space. They consist of a U-shaped bend which is activated when it is spread out and held in the spread-out manner by bending the wire or tying back the wire in a stop position against the molar teeth. This certainly does close space but also tips teeth rather than moving them bodily.

One of the more extreme configurations is described by Alan C. Brader in U.S. Pat. No. 3,593,421. This configuration called the multi-helical omni arch is basically an archwire with a series of coil spring bends incorporated between each teeth (FIG. 6). This certainly increased the resiliency of the archwire but it also decreased the amount of control available. To provide increased resiliency and still maintain control, orthodontists sometimes turned to multiple archwire fitting in multiple slots in the brackets. Atkinson's modifications of Johnson's ribbon arch bracket incorporating two archwires were mentioned above. This technique evolved into the Universal Technique which was used by a small but very enthusiastic group of professionals.

Another approach was described by Joseph Johnson in U.S. Pat. Nos. 1,952,320; 2,665,480 and 2,759,265. Johnson incorporated two small diameter archwires held together in a ribbon arch configuration with the long axis going through the two wires parallel to the long axis of the tooth (FIG. 7). U.S. Pat. No. 3,302,288 to Tepper discloses a another two-wire bracket arrangement using two parallel spaced apart crossbars interconnected by a rigid member.

The problem with all two wire techniques is the difficulty in putting in compensating bends. In theory, if the bracket of a tooth is put on the tooth in such a position that the channel of the bracket is in an ideal position, a straight archwire placed in this channel would reduce a tooth positioned in the ideal position. In actual practice, this does not happen. In the earlier days of orthodontics, the brackets were put on perpendicular to the horizontal plane of the orthodontic band. To compensate for the fact that this is not necessarily the ideal position, the orthodontist had to make compensating bends in the arch.

This problem was addressed by Dr. Larry Andrews by methods described in U.S. Pat. Nos. 3,477,128 and 3,660,900. Andrews attempted to position the slots in the bracket in such a relation to the base of the bracket that was applied to the tooth so that the slot assumed the ideal position in the average tooth. Since these brackets were generally put on the tooth by the orthodontist in the mouth using the orthodontist trained eye, errors in position were inevitable. Also, not all teeth are average and this also increases errors, so the orthodontist today must still finish cases with compensating bends.

Another twin arch approach is described by J. D. Berke in U.S. Pat. Nos. 2,406,527 and 2,705,367. Berke described a bracket which is essentially a button with two channels separated by the body of the bracket (FIG. 8). Two archwires were connected by rigid connectors between the two teeth. In one situation, the connectors were fixed and in another situation, they were slidable. The archwire was connected to the tooth by pulling the two archwires away from each other and snapping the two archwires over the bracket. The archwires returning to shape aligned the tooth. The fact that the connectors were rigid made this system very difficult to use in actual practice. It was never produced in any significant quantity commercially.

Another attempt at attaining precision with two wires was described by Northcott in U.S. Pat. No. 3,775,850. Northcott connected two and three archwires together with interarch connectors (FIG. 9). These connectors were rigid cast or brazed metal, both fixed and slidable. This rigid system was tied into corresponding slots in the labial bracket. Like Andrews, Northcott tried to eliminate the necessity for compensating bends by building the archwire slots in such a position that they were in the ideal position in the average tooth. Again, this had the problems of the Andrews system. Teeth are not always average and the operator cannot always get the bracket on the tooth in the ideal position using his eye alone. A disadvantage of Northcott's system over Andrews' system is the complete inability to put any compensating bends in the arch if the need arises.

The recently introduced NiTi wires, which are an alloy of nickel and titanium, are extremely more resilient than stainless steel. The disadvantage of these wires is the inability to readily bend the archwires. Nickel titanium archwires are usually held into shape and heat treated. This is commonly done today in the factory using preformed shapes. No compensating bends are really possible.

A number of attempts have been made to adapt the edgewise technique to lingual orthodontics. One example is disclosed in U.S. Pat. No. 4,386,908 to Kurz. A bracket based on this design as made and sold by ORMCO Corporation of Glendora, Calif. is shown in the ORMCO Catalog, page 27 (1993). The archwire is secured in this bracket by means of tie wires or elastomer O-rings. In practice, it has been found necessary to use a double-tie arrangement, with the O-rings doubled back on themselves in order to apply enough force from the O-ring to properly seat archwire in the archwire slot. Orthodontists complain that this procedure is difficult and inefficient.

Dr. Alexander J. Wildman has previously developed lingual orthodontic methods and brackets as described in U.S. Pat. Nos. 3,748,740; 3,780,437; 3,842,503; 3,854,207; 4,443,189; 4,494,931; and 5,474,444. U.S. Pat. No. 4,443,189 mentions the possibility of mounting a second or auxiliary archwire on the bracket but requires threading the second wire through the slot so its use is limited to the attachment of auxiliaries.

The lingual bracket of U.S. Pat. No. 4,443,189 has a sidable and hinged closure member that does not rely solely on the forces of the O-ring to secure the archwire in the archwire slot but also has a couple limitations. It is complicated to manufacture and requires close tolerances in its manufacture to maintain the closure dimension. The relationship of the closure member's distal end portion to the archwire slot is critical when pivoting to a closed position as shown in FIG. 2 of the patent. If the pivot position, or the tolerances of its shape, are not sufficiently precise, then the closure member's distal end portion can either close not snugly enough against the archwire or so snugly as to bind against the archwire.

Wildman has also taught a way to very accurately place the brackets on the teeth using what he calls the direct-indirect technique in U.S. Pat. No. 4,909,735. Wildman also teaches a method of custom heat treating the nickel titanium archwires into an ideal shape for each individual patient, in U.S. Pat. Nos. 5,011,406; 5,100,316; and Pat. No. 5,295,886. This shaping method opens up a number of possibilities for very complicatedly-shaped archwires which would not need compensating bends placed by the operator.

Dr. Wildman also published a history of development of lingual orthodontia and ideas for advanced lingual orthodontia including a recommended lingual bracket with a hinged closure member (FIG. 14) in "The Future of Lingual Orthodontics," *Orthodontics: Evaluation and Future,* Proceedings of the International Conference of the Orthodontic Dept. of Univ. of Nymegen, The Netherlands, Oct. 22–24, 1987, pp. 261–280 (1988). The then proposed bracket, however, still relied heavily on the forces applied by the elastomer O-ring to the secure the closure member to the bracket body and thereby retain the archwire in a two-sided notch beneath the closure member.

Accordingly, a need remains for a simpler, easier-to-use lingual orthodontic bracket and method of manufacture.

SUMMARY OF THE INVENTION

It is, therefore, an object of the invention to provide a lingual orthodontic bracket that is compatible with conventional edgewise orthodontic treatment techniques but has a more secure yet simple closure mechanism.

Another object of the invention is to provide a lingual orthodontic bracket that is easy to latch and unlatch while the archwire is being adjusted.

Another object is to simplify the manufacture and operation of lingual orthodontic brackets.

A first aspect of the invention is an improved lingual orthodontic bracket which includes a bracket body having a three-sided archwire slot and a hinged closure member pivotable across the archwire slot between open and closed positions, the closure member having a closure portion which extends across the archwire to retain the archwire in the slot under shear in the closed position. Preferably, the bracket includes two oppositely directed wings formed respectively on the bracket body and the closure member for receiving a ligature or O-ring to secure the closure member in the closed position.

The bracket body is shaped to form a base that can be affixed to a tooth surface via a bonding pad. An archwire slot is formed in the body, oriented at an acute angle, for example in a range of about a 45° to 65° angle to the base. Preferably, the bonding pad can be connected to the bracket body and the bonding pad angled to properly orient the archwire slot. The bracket body preferably includes a hook or wing extending away from the archwire slot at an angle roughly parallel to the plane of the bonding pad. The hinge is formed in the bracket body on a side of the archwire slot opposite the hook or wing. The hinge can include a laterally extending hook or J-shaped extension for application of intermaxillary elastics.

The closure member is a substantially rigid member formed in a generally J-shape having a first distal end connected pivotally by the hinge to the bracket body, a second distal end preferably forming a hook or wing oppositely directed from the hook of the bracket, and a central portion shaped so as to extend across the archwire slot in the closed position to retain the archwire seated in shear in the archwire slot.

In a second aspect of the invention, the central portion of the closure member is formed with a shape that exerts a camming force on the archwire to seat it in the slot as the closure member is rotated toward the closed position. This provides substantial mechanical advantage during closure and in treatments that do not permit immediate complete seating of the archwire in the slot. The hinge and closure member are also preferably formed to provide an over-center action upon closure so that only minimal force need be provided to keep the closure member closed against the forces of the archwire.

In another aspect of the invention, the bracket body includes a closure member slot positioned to receive a retainer portion of the second distal end of the closure member when the closure member is in a closed position. The closure member is substantially planar and the retainer portion of the second distal end includes a protrusion which deviates from the plane of the closure member, and the closure member slot has substantially parallel sidewalls. The closure member slot can include an enlarged entrance and/or a divergent portion for receiving the protrusion of the closure member. The divergent portion of the closure member slot can be a hole oriented generally normal to the archwire slot, the hole communicating along its axis with the closure member slot.

In a further aspect of the invention, the bracket body includes a closure member slot positioned to receive a retainer portion of the second distal end of the closure member when the closure member is in a closed position and the retainer portion of the closure member can be bent such that, when the closure member is rotated into the closed position, the retainer portion wedges in the closure member slot thereby holding the closure member in the closed position.

In yet another aspect of the invention, the bracket body has a top surface, and the enlarged entrance of the closure member slot includes a groove in the top surface of the body, the groove communicating along its length with the closure member slot.

In both the second and third embodiments, the closure member can include a notch sized to admit a tool for releasing the closure member from the closed position within the closure member slot.

The foregoing and other objects, features and advantages of the invention will become more readily apparent from the following detailed description of a preferred embodiment of the invention which proceeds with reference to the accompanying drawings.

BRIEF DESCRIPTION OF THE DRAWINGS

FIG. 4 is a plan view to scale of the body of the bracket of FIG. 1 at an intermediate stage of manufacture.

FIG. 5 is a plan view of the closure member of the bracket of FIG. 1 at an intermediate stage of manufacture.

FIG. 6 is a plan view to scale of the bonding pad of the bracket of FIG. 1 at an intermediate stage of manufacture.

FIG. 14 is a top plan view of the bracket body of FIG. 10.

FIG. 15 is a sectional view taken along lines 15—15 in FIG. 14.

FIG. 16 is a front elevation view of the bracket body of FIG. 10.

FIG. 17 is a front elevation view of a third embodiment of a lingual orthodontic bracket in accordance with the present invention.

FIG. 18 is a top plan view of the bracket of FIG. 17.

FIG. 19 is a sectional view taken along lines 19—19 in FIG. 18 showing the overall operation of the bracket.

FIG. 26 is a side elevation view of the bracket body of FIG. 20 with details of the archwire bumper spring shown in dashed lines.

FIG. 27 is a top plan view of the archwire bumper spring of FIG. 26 shown in a pre-folded state.

FIG. 28 is a front elevation view of the archwire bumper spring of FIG.26.

FIG. 29 is a top plan view of the archwire bumper spring of FIG.26 in relation to the archwire.

FIG. 31 is a top plan view of the bracket of FIG. 30, omitting the archwire rotating or bumper springs and bonding pad.

FIG. 32 is a side elevation view of the bracket of FIG. 30.

FIG. 33 is a bottom plan view of the bracket of FIG. 30, omitting a portion of the archwire rotating or bumper springs and the bonding pad.

FIG. 34 is an elevation view of the bracket taken lines 34—34 in FIG. 32.

DETAILED DESCRIPTION

First Embodiment

Figure 1:
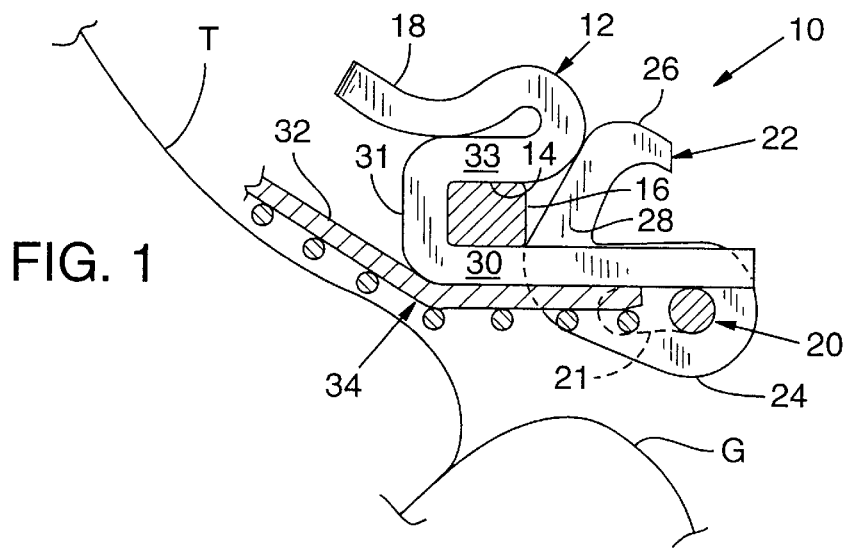
FIG. 1 is a side elevation view of a first embodiment of a lingual orthodontic bracket in accordance with the invention.
Figure 2:
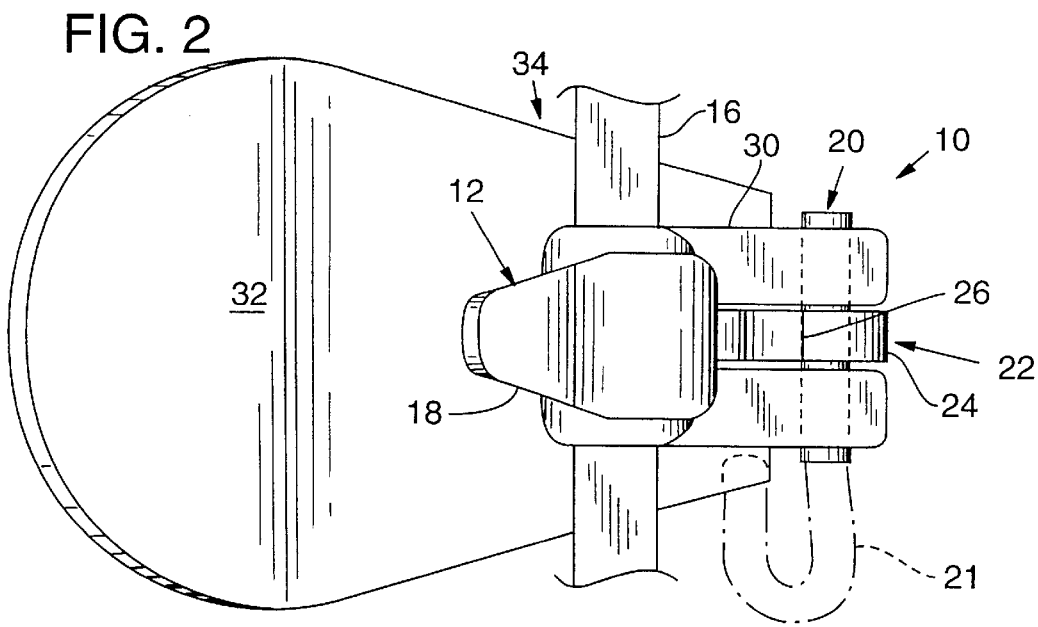
FIG. 2 is a top plan view of the bracket of FIG. 1.
Figure 3:
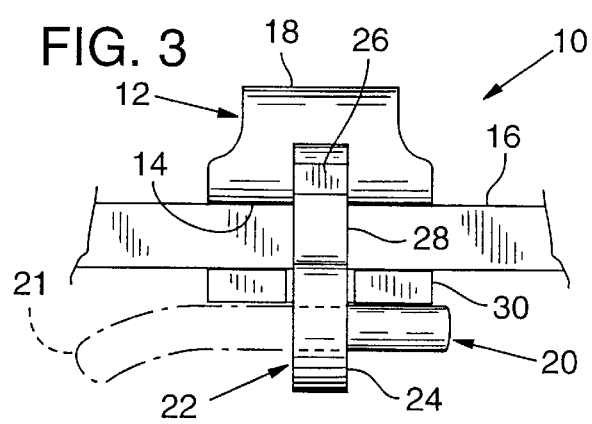
FIG. 3 is a front elevation view of the bracket of FIG. 1.

FIGS. 1–3 respectively show a first embodiment of a lingual bracket 10 in accordance with the invention. The bracket includes a bracket body 12 having a three-sided archwire slot 14 for receiving an archwire 16. A first tie wing 18 is formed in the bracket body and oriented to extend in a first direction away from the archwire slot on a first side thereof for receiving a loop of a tie wire or elastomer O-ring. A hinge pin 20 is mounted on the bracket body on a second side of the archwire slot, opposite the first tie wing and extending parallel to the archwire slot.

A closure member 22 is pivotably connected to the bracket body by means of a cylindrical distal end 24 rotatably connected to hinge pin 20 so as to swing closure member 22 across the archwire slot 14. The closure member is a substantially rigid member having a generally J-shape. The closure member includes the first or proximal end 24 connected pivotally by the hinge pin 20 to the bracket body, a second, hook-shaped distal end forming a second tie wing 26 oppositely directed from the first tie wing 18, and a central, cam shaped portion 28 arranged to extend across the archwire slot 14 to retain the archwire 16 seated in shear in the archwire slot when closed.

The bracket body is formed with a base layer 30 that can be affixed to a bonding pad 32 for mounting the bracket on a tooth T at a position occlusally spaced from gingiva G. The base layer 30 forms a first sidewall of three walls defining the archwire slot 14. The bracket body also has a bottom wall 31 extending normal to the base layer 30 and an opposite sidewall 33 extending parallel to sidewall 30 and normal to the base wall 31 to define the other two walls of the slot 14.

The hinge is formed by brazing the hinge pin 20 to the underside of base layer 30 of the bracket body on a side of the archwire slot opposite the tie wing 18. The hinge pin can include a laterally extending hook or J-shaped extension 21 for application of intermaxillary elastics.

The bonding pad 32 is connected to the underside of the bracket body 12 along base layer 30 and the bonding pad is obtusely angled along bend line 34 to orient the sidewalls of archwire slot 14 approximately parallel to the patient's occlusal plane. The base layer 30 (optionally wedge-shaped) and bonding pad 32 together form a base for the bracket. The archwire slot is thus oriented at an acute angle, for example, in a range of a 45° to 65° angle to the portion of the bonding pad 32 extending forward from the base layer 30. The bracket body tie wing 18 extends away from the archwire slot 14 at an angle roughly parallel to the plane of the bonding pad.

Referring to FIG. 4, the bracket body is preferably formed by chemically etching a layer of heat-treatable steel, such as 17/7 stainless steel, of 0.012 inch (0.30 mm) thickness to the shape shown in FIG. 4, bent to the shape shown in side view in FIG. 1, and then brazed, using the method described in my prior U.S. Pat. No. 5,154,606. Alternatively, a similarly-shaped bracket body can be formed by other techniques including machining, investment casting or injection molded powder metal technologies. Base layer 30 is bent at a right angle to bottom wall portion 31 along bend line 40, which is in turn bent at a right angle to top wall portion 33 along bend line 42. Optionally, the bends 40, 42 can be die-formed simultaneously. The wing portion 18 is then folded along bend line 44 and optionally recurved as shown in FIG. 1. Then, the parts are cut from the strip of metal from which they were originally etched. Up to this point, the hinge pin 20 has not been mounted on the bracket body.

The closure member is also preferably formed by the technique described in my prior U.S. Pat. No. 5,154,606 as shown in FIG. 5, but could also be made using the other methods mentioned above. The closure member is made with two layers 22A, 22B of, e.g., 0.008 inch (0.20 mm) thick 17/7 stainless steel, to facilitate chemical etching of the holes 46A, 46B that receive the hinge pin 20. The layers and holes are formed to the shapes shown in FIG. 5 and are temporarily spot-welded together using alignment pins in the carrying strips. The layers 46A, 46B are brazed together and then they are cut off along cutting line 48.

Next, the bracket body is positioned on the bonding pad, which has been chemically etched in mesh-foil to the shape shown in FIG. 6 or other suitable shape, and the closure member and hinge pin are assembled with pin 20 received in holes 46A, 46B and positioned along the underside of base layer 30 of the bracket body. This assembly is preferably done using an assembly jig to hold all parts in their proper position. Then the parts are tack-welded together (the bracket body to the bonding pad, the hinge pin to the base layer) and then hydrogen brazed. Finally, the bonding pad is cut off its carrying strip. This assembly technique can be varied to suit different manufacturing preferences.

Figure 7:
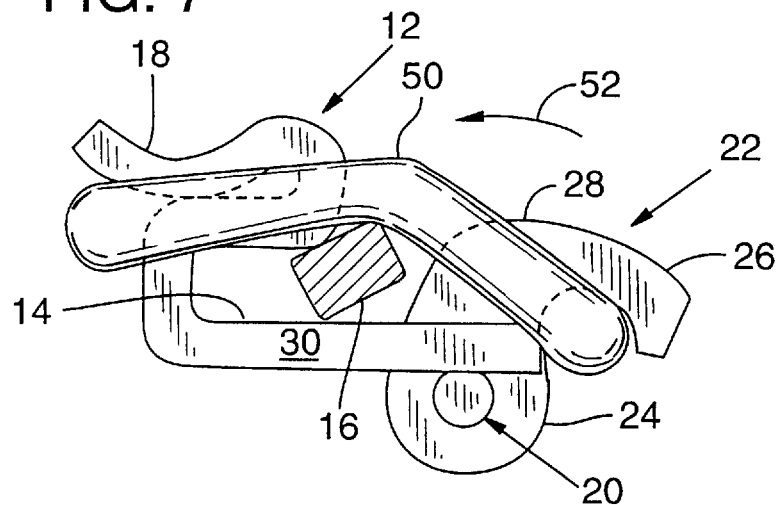
FIGS. 7 and 8 are side elevation views similar to FIG. 1 showing the overall operation of the bracket.

FIG. 7 shows the initial steps of inserting an archwire 16 into the mouth of archwire slot 14 ( i.e., partially but not completely into the archwire slot since the orthodontist might not be able to completely seat the resilient archwire in the slot) and then applying an elastomer O-ring 50 over the tie wings 18, 26. This action rotates the closure member 22 toward the archwire slot 14 about hinge pin 20 as indicated by arrow 52. As the central portion 28 of the closure member engages a side of the archwire 16, continued rotation of the closure member tends to drive the archwire into the slot 14. As further described below, the central portion 28 of the closure member is cam shaped, with a convex outer surface formed as a positive rotational cam to obtain a mechanical advantage from contraction of the O-ring to seat the archwire forcibly into the archwire slot, as indicated by arrows 54 and 56 in FIG. 8. Additionally, it is preferred to have the central portion 28 of the closure member formed with at least a constant curve defining a neutral cam along a portion of its surface so that, once the archwire is fully seated in the slot, any force or attempted movement of the archwire out of the slot is exerted radially through the closure member against hinge pin 20. This action resists the forces thereby maintaining the closure member across the archwire slot. This action can be enhanced by forming the central portion 28 with an over-center or retrograde cam shape that tends to increase the holding force as next described.

Figure 9A:
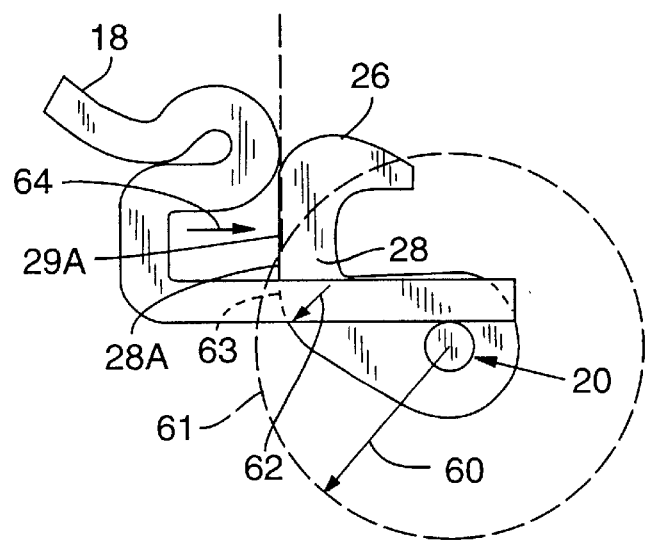
FIGS. 9A, 9B and 9C are side elevation views similar to FIG. 1 showing details of construction and operation of the closure member.

FIG. 9A shows the initial camming action which seats the archwire in the archwire slot. The central portion 28 of the closure member in general rotates about hinge 20 through a first arc 61 having a first radius 60, e.g., 0.050 inches (1.27 mm), and the central portion itself has an outer surface which is convexly curved about a smaller radius 62, e.g., 0.016 inches (0.41 mm), that is tangential to the first arc at location 28A. This shape provides a positive camming surface along arc 63 in central portion 28 which progressively advances toward the archwire slot until the tangent point 28A between the two arcs is reached. This arrangement, as thus far described, exerts a positive camming force on the archwire to seat it in the slot as the closure member is rotated toward the closed position. It provides substantial mechanical advantage during closure and in treatments that do not permit immediate complete seating of the archwire in the slot. At point 28A, the camming action to seat the archwire in the slot ceases.

The closure member is preferably shaped, and the base layer 30 is slotted, to permit the closure member to continue to be rotated for an additional distance past point 28A to surface segment 29A (surface segments 29B and 29C in FIGS. 9B and 9C, respectively) of central portion across the archwire slot which does not cross arc 61 as shown in FIG.

Figure 9B:
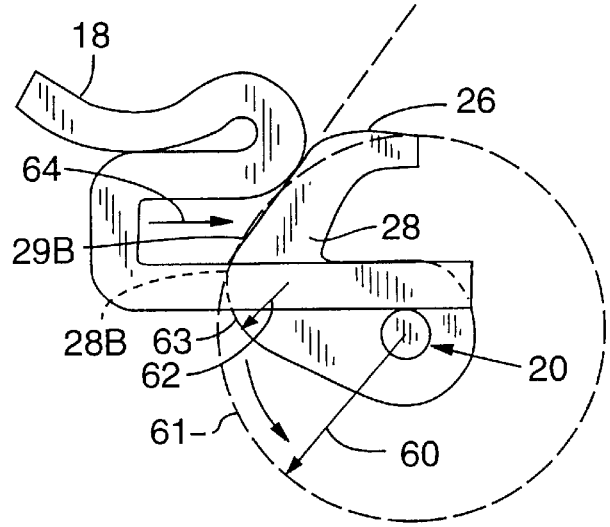
Figure 9C:
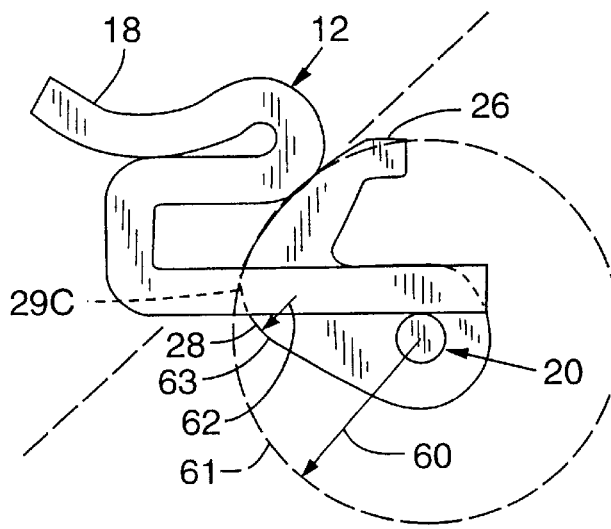
Figure 10:
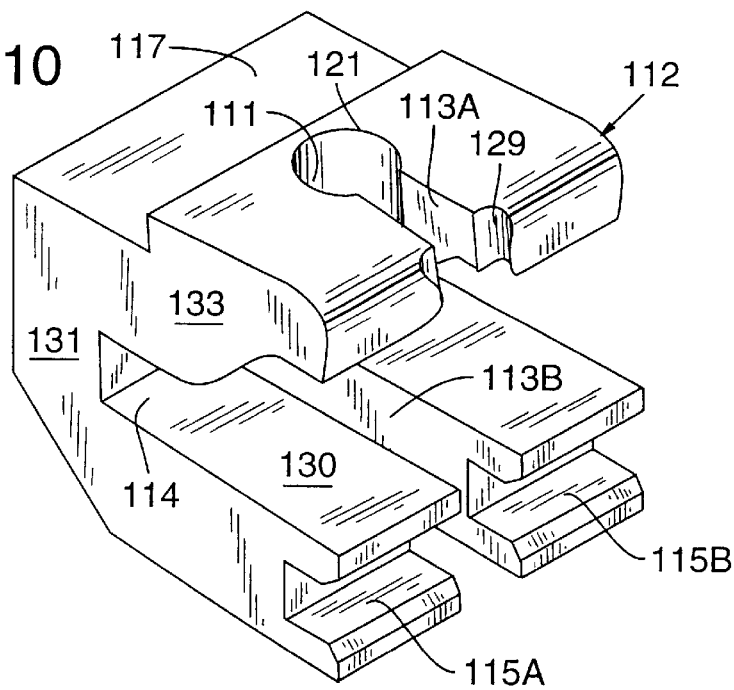
FIG. 10 is a perspective view of a lingual orthodontic bracket body in accordance with a second embodiment of the present invention.

9A but either coincides with arc 61 (on center) as shown in FIG. 9C or is even slightly retrograde from arc 61 (over center) as shown in FIG. 9B. What this means is that, once the seating cam surface is passed (segment 63), the tangential surface above points 29C or 29B can either be neutral in its camming action as shown in FIG. 9C (i.e., the radius of the surface above point 29C is equal to the radius 60 of rotation of portion 28 about the hinge pin) or can be negative (i.e., the radius of the surface above point 29B is less than radius 60) as in FIG. 9B. Either of these configurations will effectively resist removal forces on the archwire (arrow 64) and both are preferred over the configuration of FIG. 9A, although the negative configuration of surface segment 29B in FIG. 9B will actually tend to actively retain the closure member in the closed position.

Thus, in addition to the positive camming action to help initially seat the archwire 16 in the slot 14, the hinge 20 and closure member 22 are also preferably positioned and formed to provide a neutral or over-center action upon closure so that only minimal force need be provided by the O-ring 50 to hold the wings 18, 26 together against forces tending to unseat the archwire from slot 14.

Second Embodiment

FIGS. 10–16 show a second embodiment of a lingual bracket 110 in accordance with the present invention. This embodiment is shown as a machined or cast part. The bracket includes a bracket body 112 having a three-sided archwire slot 114 for receiving an archwire 116. The bracket body 112 includes a base layer 130 which forms a first sidewall of three walls defining the archwire slot 114. The bracket body has a bottom wall 131 extending normal to the base layer 130 and an opposite sidewall 133 extending parallel to base layer 130 and normal to the bottom wall 131 to define the other two walls of the slot 114.

The bracket body also has a first closure member slot 113A formed in opposite sidewall 133 and a second closure member slot 113B formed in base layer 130 for receiving a closure member 122. The first and second closure member slots 113A and 113B, which are substantially coplanar to each other, are preferably oriented substantially normal to the archwire slot 114.

The bracket body preferably includes a first tie wing 118 which is formed by brazing a tie wing plate 119 into a recessed portion 117 of the bracket body and is oriented to extend away from the archwire slot on a first side thereof for receiving a loop of a tie wire or elastomer O-ring. A hinge pin 120 is mounted in hinge pin slots 115A and 115B in the bracket body on a second side of the archwire slot, opposite the first tie wing 118 and extending parallel to the archwire slot 114. The hinge is formed by brazing or crimping the hinge pin 120 into the hinge pin slots 115A, 115B.

Figure 13:
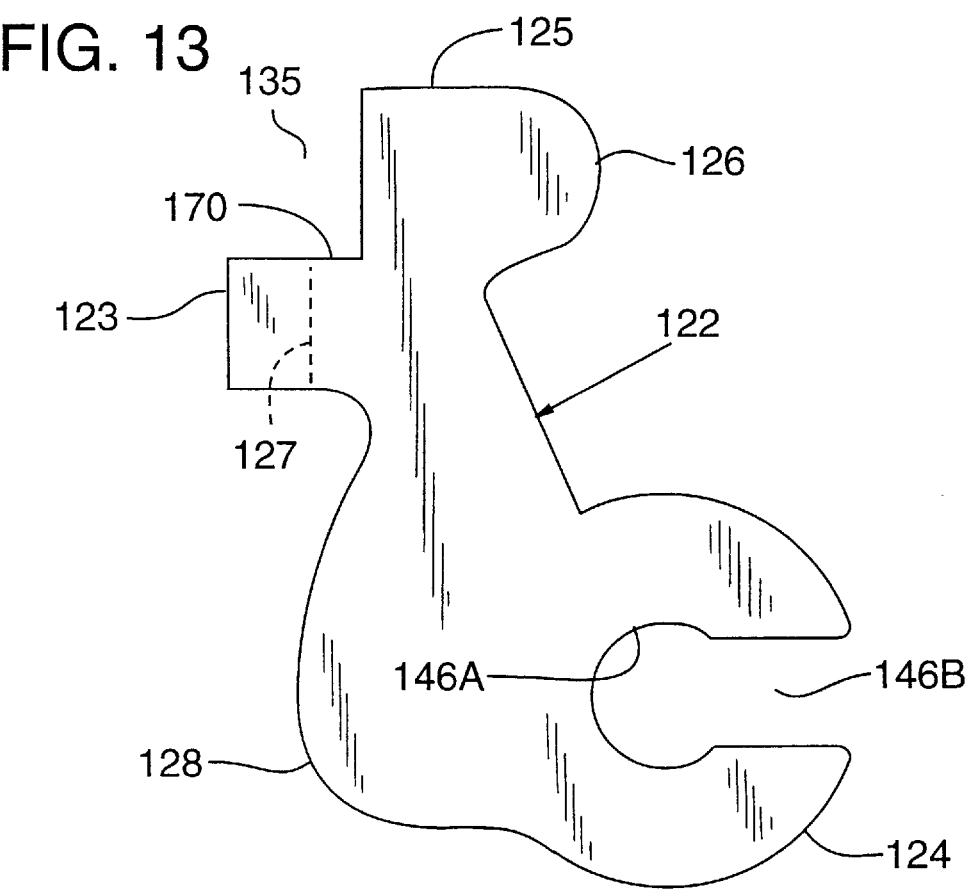
FIG. 13 is a side view of the closure member of the bracket of FIG. 11.
Figure 20:
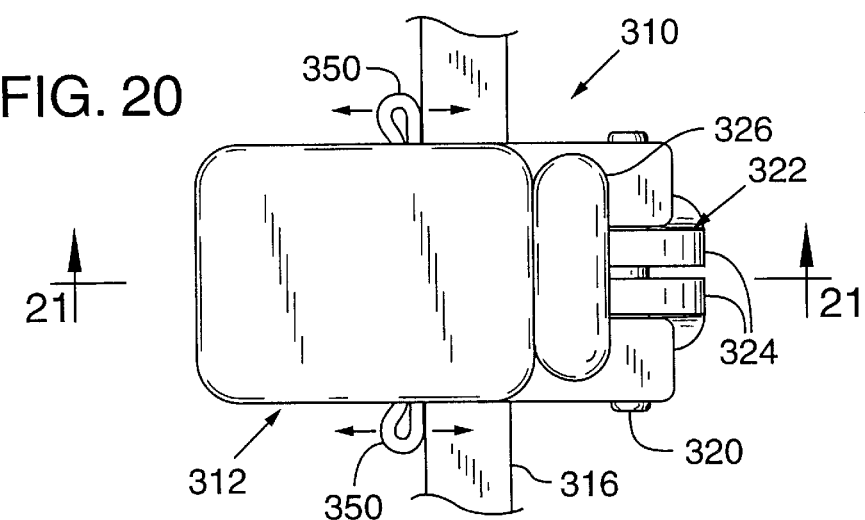
FIG. 20 is a top plan view of a further embodiment of a lingual orthodontic bracket according to the invention.

The closure member 122, best shown in FIG. 13, includes a first distal end 124 having a hole 146A. The closure member is pivotally connected to the bracket body by hinge pin 120 which passes through hole 146A so that the closure member swings into the closure member slots 113A, 113B and across the archwire slot 114. The first end of the closure member preferably includes a keyhole shaped channel 146A,146B which allows the closure member to snap onto the hinge pin. The closure member also includes a second distal end 125 and a central, cam shaped portion 128 arranged to extend across the archwire slot 114 to retain the archwire 116 seated in shear in the archwire slot when closed. The second distal end 125 preferably includes a second tie wing 126 oppositely directed from the first tie wing 118. The first distal end and the central cam shaped portion give the closure member a generally J-shape.

Figure 11:
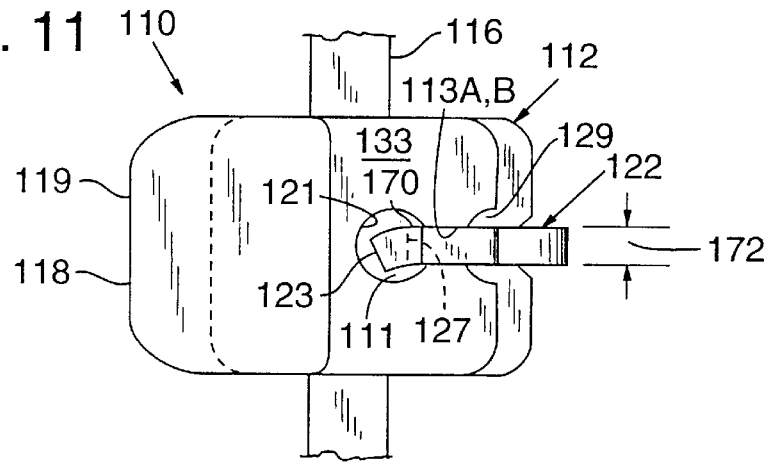
FIG. 11 is a top plan view of a lingual orthodontic bracket including the bracket body of FIG. 10.

The closure member 122 is a substantially planar member made from a resilient material such as $^{17}/_{7}$ stainless steel. The closure member of this embodiment includes a retainer portion or tab 170 which is bent or angled along bend line 127 to form a protrusion 123 which deviates from the principal plane of the closure member as shown in FIG. 11. The protrusion can also be formed by embossing a dimple in the retainer portion, depositing a droplet of solder, welding a bead of filler metal, or any other suitable technique.

Preferably, the first closure member slot 113A has an enlarged entrance 129 and a divergent portion 111 formed by a portion of a cylindrical hole 121 which communicates with the closure member slot 113A and is oriented generally normal to the archwire slot. When the closure member is rotated into the closure member slot, as shown by the arrow 180 in FIG. 12B, the retainer portion 170 enters the enlarged opening 129 and is guided into the closure member slot 113A.

Figure 12A:
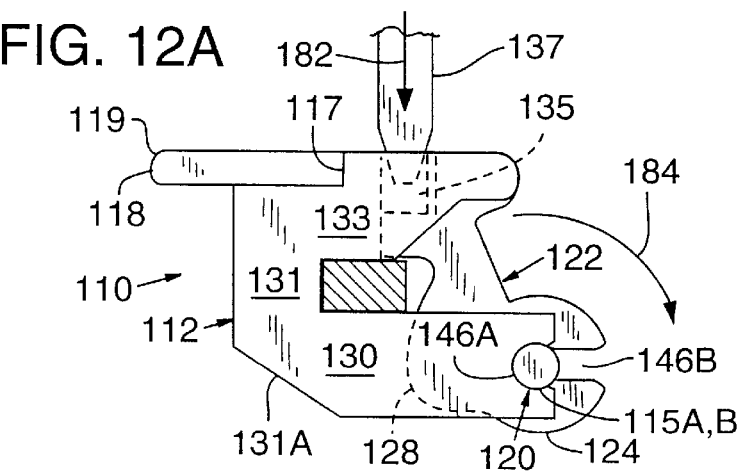
FIGS. 12A and 12B are side elevation views of the bracket of FIG. 11 showing the overall operation of the bracket.
Figure 12B:
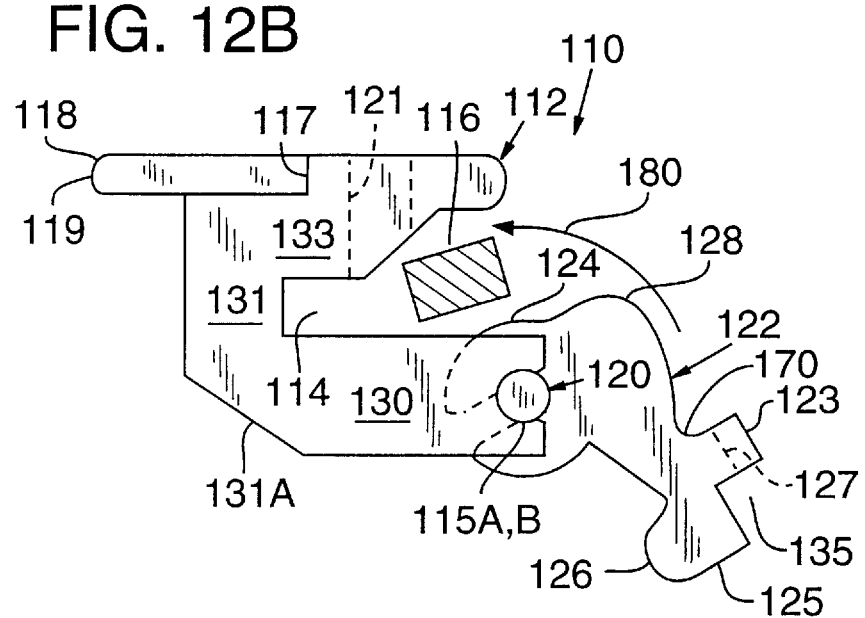

Referring to FIG. 11, the resilient material used for the closure member has a thickness 172 which, as an example, can be 0.012 inch (0.30 mm). Referring to FIG. 14, the closure member slot has a width 174 which, as an example, can be 0.014 inch (0.36 mm). The thickness of the closure member is chosen to be only slightly smaller than the width of the closure member slot so that the protrusion 123 or the bracket body 112 must flex in order for the closure member to completely enter the closure member slot and reach the closed position as shown in FIG. 12A. When the closure member reaches the closed position, the protrusion 123 or the bracket body 112 relaxes and the protrusion engages the divergent portion 111 of slot 113A thereby latching the closure member in the closed position. Bend line 127 is preferably oriented parallel to the hole 121 when the closure member is in the closed position.

Referring to FIG. 13, the closure member 122 preferably includes a notch or recess 135 located at the second distal end 125. The notch 135 allows for insertion of a tool 137 into the closure member slot between the bracket body and the closure member which tool can then be used to force the closure member out of the closure member slot as shown by the arrows 182, 184 in FIG. 12A.

Figure 8:
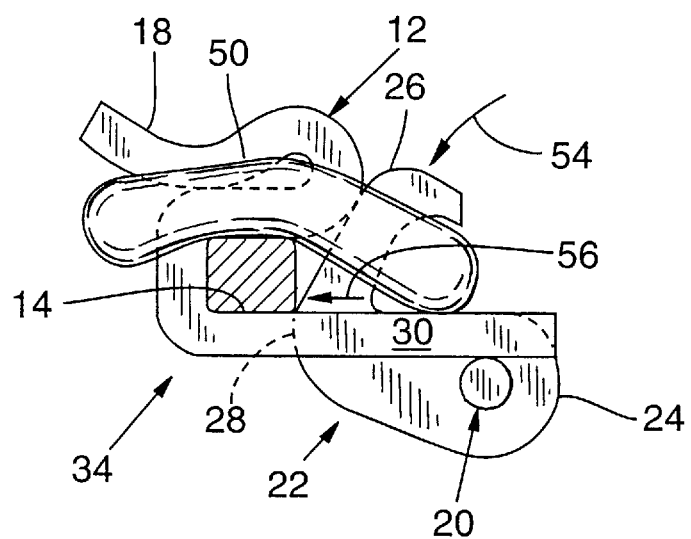

An elastomer O-ring can be applied over the tie wings 118 and 126 to rotate the closure member into the closed position as discussed above with relation the first embodiment as shown in FIGS. 7 and 8. The central portion 128 of the closure member is cam shaped, with a convex outer surface formed as a positive rotational cam to obtain a mechanical advantage from contraction of the O-ring to seat the archwire forcibly into the archwire slot. Additionally, it is preferred to have the central portion 128 of the closure member formed with at least a constant curve defining a neutral cam along a portion of its surface so that, once the archwire is fully seated in the slot, any force or attempted movement of the archwire out of the slot is exerted radially through the closure member against hinge pin 120. This action resists the forces thereby maintaining the closure member across the archwire slot. This action can be enhanced by forming the central portion 128 with an over-center or retrograde cam shape that tends to increase the holding force. The closure member can be shaped in various ways to resist removal of the archwire as previously discussed with reference to FIGS. 9A–9C for the first embodiment.

Referring to FIGS. 13 and 15, the bracket body 112 has a bottom surface 131A for attaching the bracket body to a bonding pad. The bottom surface 131A is angled so as to orient the opposing sidewalls 130 and 133 of the archwire slot at an acute angle to the bonding pad, for example 45 deg. to 60 deg. The bottom surface 131A also includes a channel oriented generally normal to the archwire slot. The first tie wing 118 is thus oriented at the same acute angle with respect to the bonding pad. The bonding pad 132 can then be used to mount the bracket on a tooth T in the manner shown for the first embodiment in FIG. 1 as previously discussed.

The bracket body 112 can be formed by any suitable technique including machining, investment casting or injection molded powder metal technologies. The closure member is preferably formed by die stamping or chemical etching.

Third Embodiment

FIGS. 17–19 show a third embodiment of a lingual bracket 210 in accordance with the present invention. This embodiment resembles the second embodiment but has a somewhat different arrangement of the closure member and closure member slot.

The bracket includes a bracket body 212 having a three-sided archwire slot 214 for receiving an archwire 216. The bracket body 212 includes a base layer 230 which forms a first sidewall of three walls defining the archwire slot 214. The bracket body also has a bottom wall 231 extending normal to the base layer 230 and an opposite sidewall 233 extending parallel to base layer 230 and normal to the bottom wall 231 to define the other two walls of the slot 214.

The bracket body has a first closure member slot 213A formed in opposite sidewall 233 and a second closure member slot 213B formed in base layer 230 for receiving a closure member 222. The first and second closure member slots 213A and 213B, which are substantially coplanar to each other, are preferably oriented substantially normal to the archwire slot 214.

The bracket body preferably includes a first tie wing 218 formed by a tie wing plate 219 in a recessed portion 217. A hinge pin 220 is mounted in hinge pin slots 215A and 215B in the bracket body on a second side of the archwire slot, opposite the first tie wing 218 and extending parallel to the archwire slot 214.

The base layer 230 can be affixed to a bonding pad 232 for mounting the bracket on a tooth T at a position occlusally spaced from gingiva G as previously discussed with respect to the first embodiment as shown in FIG. 1.

The closure member 222 includes a first distal end 224 having a hole 246A. The closure member is pivotally connected to the bracket body by a hinge pin 220 which passes through hole 246A so that the closure member swings into the closure member slots 213A, 213B and across the archwire slot 214. The first end of the closure member preferably includes a keyhole shaped channel 246A, 246B which allows the closure member to snap onto the hinge pin. The closure member also includes a second distal end 225 and a central, cam shaped portion 228 arranged to extend across the archwire slot 214 to retain the archwire 216 seated in shear in the archwire slot when closed. The second distal end 225 preferably includes a second tie wing 226 oppositely directed from the first tie wing 218.

The closure member 222 is a substantially planar member made from a resilient material such as 17/7 stainless steel. The closure member of this embodiment includes a retainer portion or tab 270 which is bent or angled along bend line 227 to form a protrusion 223 which deviates from the principal plane of the closure member as shown in FIG. 17.

The protrusion can also be formed by embossing a dimple in the retainer portion, depositing a droplet of solder, welding a bead of filler metal, or any other suitable technique.

Preferably, the first closure member slot 213A has an enlarged entrance 229 formed by a groove in the top surface 233A of the sidewall 233 which communicates along its length with the first closure member slot 213A. Referring to FIG. 17, the groove and the closure member slot form a ridge 278 in the bracket body. When the closure member is rotated into the closure member slot the retainer portion 270 enters the enlarged opening 229 and is guided into the closure member slot.

Referring to FIG. 17, the resilient material used for the closure member has a thickness 272 which, as an example, can be 0.012 inch (0.30 mm). The closure member slot has a width 274 which, as an example, can be 0.014 inch (0.36 mm). The thickness of the closure member is chosen to be only slightly smaller than the width of the closure member slot so that the protrusion 223 or the bracket body 212 must flex in order for the closure member to completely enter the closure member slot and reach the closed position as shown in FIG. 19. When the closure member reaches the closed position, the protrusion 223 remains wedged in the closure member slot 213A, thereby holding the closure member in the closed position. Bend line 227 is preferably oriented parallel to the groove in the top surface 233A of the sidewall 233 and is below the ridge 278 a distance 276 when the closure member is in the closed position.

Referring to FIG. 19, the closure member 222 preferably includes a notch or recess 235 located at the second distal end 225. The notch 235 allows for insertion of a tool 237 into the closure member slot which can then be used to force the closure member out of the closure member slot as shown by the arrows 282 and 284 in FIG. 19.

An elastomer O-ring can be applied over the tie wings 218 and 226 to rotate the closure member into the closed position as discussed above with relation to the first embodiment as shown in FIGS. 7 and 8. The central portion 228 of the closure member is cam shaped, with a convex outer surface formed as a positive rotational cam to obtain a mechanical advantage as previously discussed with relation to the first embodiment.

As with the second embodiment, the closure member 222 of the third embodiment can be shaped in various ways to resist removal of the archwire as previously discussed with reference to FIGS. 9A–9C for the first embodiment.

Referring to FIG. 19 the bracket body 212 has a bottom surface 231A for attaching the bracket body to a bonding pad 232. The bottom surface 231A is angled so as to orient the opposing sidewalls 230 and 233 of the archwire slot at an acute angle to the bonding pad. The bottom surface 231A also includes a channel oriented generally normal to the archwire slot. The first tie wing 218 is thus oriented at the same acute angle with respect to the bonding pad. The bonding pad 232 can then be used to mount the bracket on a tooth T in the manner shown for the first embodiment in FIG. 1 as previously discussed.

Figure 21:
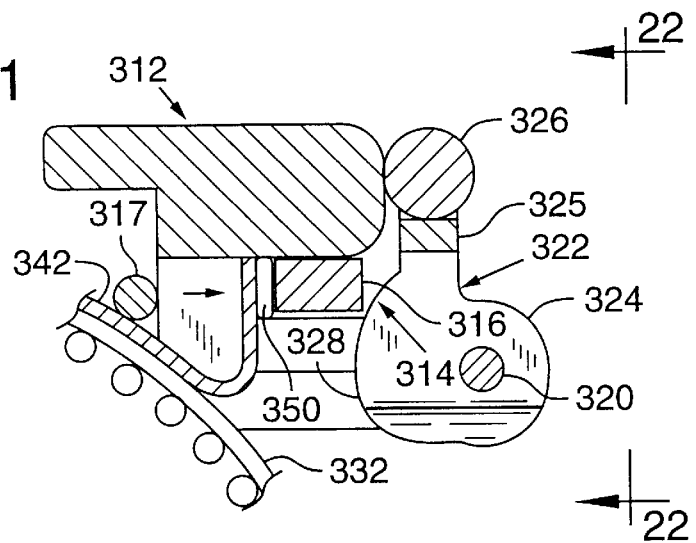
FIG. 21 is a cross-sectional view taken along lines 21—21 in FIG. 20.
Figure 22:
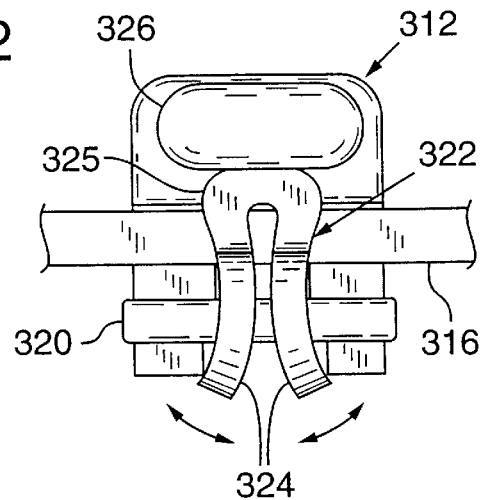
FIG. 22 is a cross-sectional view taken along lines 22—22 in FIG. 21.

FIGS. 20–25 show an alternative design of the bracket 310 which lack the closure slot and associated structure of the previous embodiment; has a somewhat different shape of distal end of the closure member, and employs a novel spring structure as an archwire bumper. The general arrangement of the bracket body 312 is the same, as are the closure member first distal end and hinge 320, 324, and the central camming portion 328 is unchanged in side view, so these parts will not be further described. The closure member body is formed in two layers in this embodiment, as best seen in FIG. 22, by folding over at the second distal end 325. The second distal end 325 has a cylindrical bar 326 mounted to form a T-shaped end on the closure member in a position parallel to the archwire slot 314 and archwire 316. FIG. 21 also shows an optional auxiliary archwire 317 positioned in a notch formed between the back wall of the bracket body and the bonding pad.

Mounted in the base of the archwire slot 314, in position between the archwire and the bottom wall of the slot, is a bumper spring 340 best seen in FIGS. 26–29. FIG. 27 shows the spring 340A in a flat, T-shape at an intermediate stage in manufacture. Following bending, the spring has the shape shown in FIGS. 26, 28 and 29. The tail portion 342 of the T is bent to an L-shape as shown in FIG.26 at bend line 344 and, after brazing the bracket body to the bonding pad 332, is tack welded to the pad at weld spot 345. The wings 346 of the spring are bent at bend lines 348 to form folded end portions 350. These end portions resiliently cushion the arch wire 316 when it is pressed into the archwire slot 314 by the closure member 322.

Figure 23:
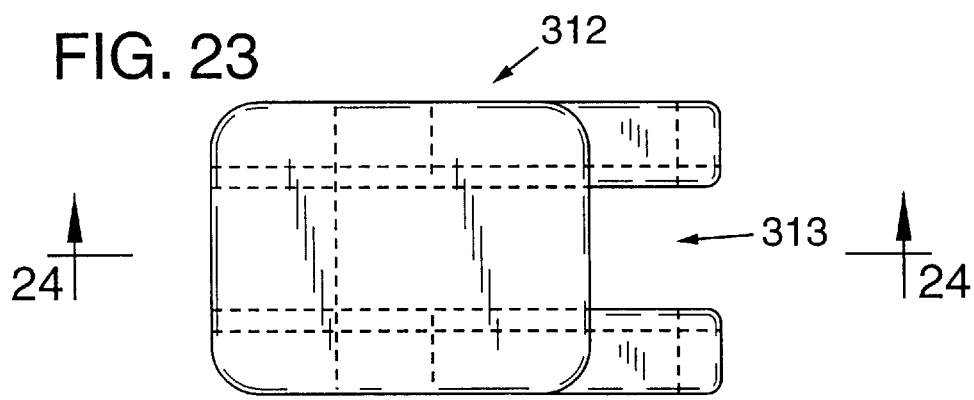
FIG. 23 is a top plan view of the body of the bracket of FIG. 20.
Figure 24:
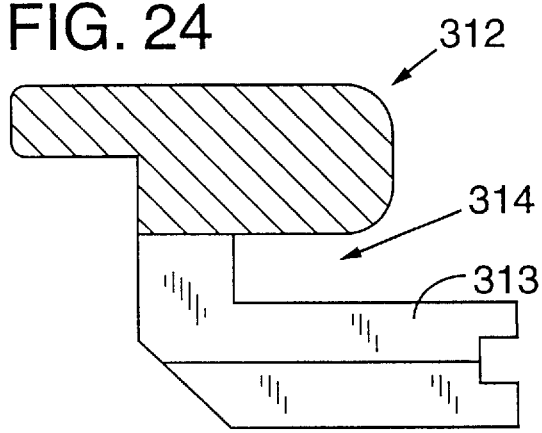
FIG. 24 is a cross-sectional view taken along lines 24—24 in FIG. 23.
Figure 25:
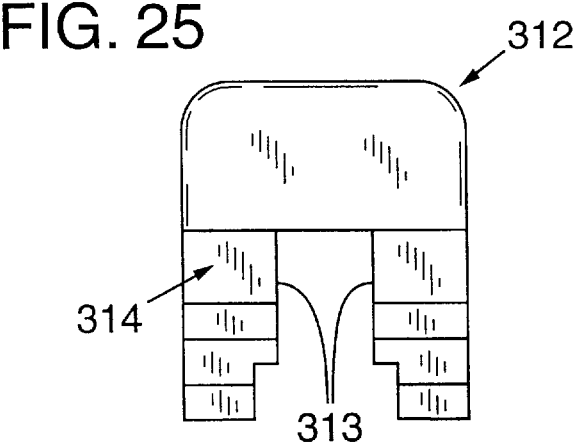
FIG. 25 is a front elevation view of the bracket body of FIG. 20.

FIGS. 23–25 show the bracket body 312 at an intermediate stage of assembly. As noted above, the overall structure is similar to the other versions, and so need not be described in great detail. The principal difference is that, to utilize spring 340, the bracket body is formed with an internal channel or slot 313 extending to the back side of the bracket body. The tail portion 342 of the spring is sized to the width of slot 313. The slot 313 extends upward behind the archwire slot 314 to permit the spring to flex more freely behind the archwire.

Fourth Embodiment

FIGS. 30–34 show another, presently preferred, alternative design of the bracket, generally denoted by reference numeral 410. Bracket 410 also lacks a closure slot but includes an alternative means for interengaging the closure member and the bracket body to retain the closure member in the closed position. This embodiment has a bracket body 412 whose general arrangement is similar to that of the above-described embodiments, and the closure member 422 shows, in side view, a shape resembling in most of its principal respects, those of the previously-described embodiments. As much as possible, the same reference numerals as previously used above are shown on the drawings of bracket 410, with a first digit 4 preceding the common parts of the reference numbers.

The principal difference between bracket 410 and those previously described is that the closure member 422 is formed with first and second lateral side portions, 424A, 428A and 424B, 428B, which are spaced apart to straddle the bracket body. Accordingly, the hinge pin, secured to the bracket body by a tab 415 and brazing (see FIG. 33) extends through the first distal end portions 424A, 424B, which are positioned on opposite sides of the base portion 430 of the bracket body. The closure member 422 similarly has two spaced-apart central portions 428A, 428B positioned to span the archwire slot 414, along opposite sides 433 of the bracket body. The second distal end 426 of the closure member is formed in a generally U-shape to interconnect the first and second side portions. As in the previously disclosed brackets, the bracket body preferably includes a first tie wing 418 on a side of the bracket body opposite the hinge 420. The second distal end 426 of the closure member 422 is correspondingly shaped to form a second tie wing extending away from the bracket body, that is, in the opposite direction of tie wing 418.

Each lateral side portion of the closure member 422 includes a locking ear portion 425A, 425B protruding inward toward each opposite lateral or side face of the bracket body 412. Although these locking ears could be formed in the second distal end portion 426, where it contacts the upper portion of bracket body 412, the locking ears 425A, 425B are preferably positioned between the first camming surface portion of the central portion 428A, 428B and the first distal end 424A, 424B of the closure member. In general, the locking ear portions are positioned to engage interferingly with opposite side faces of the bracket body such that, when the closure member is rotated into the closed position (as indicated by arrow 452 in FIG. 30), the locking ear portions engage the side faces of the bracket body to hold the closure member in a closed position. With the locking ears 425A, 425B, in their preferred position, near the hinge 420, they engage the side faces of the bracket body along the lower portion or base 430 of the bracket body. The locking ear portions and side faces of the bracket body are mutually positioned and arranged to interengage through a limited angle, preferably coinciding with the exertion of the positive camming force by the central portion of the closure member against the archwire. The side faces of the bracket body are relieved to form a corner or shoulder, preferably along the lower edge of base portion 430, to receive the locking ear portions when the closure member is fully closed.

As the closure member is moved from an open to a closed position, it begins to exert a positive camming force on the archwire to seat it more deeply in the archwire slot. As the closure member 422 is pivoted toward an increasingly closed position, the locking ears 425A, 425B, interferingly engage the sides of bracket body base 430. As the closure member reaches a position in which the archwire is fully seated in slot 414, the locking ears break over the lower shoulder of base portion 430. In this position, a combination of spring force of the lateral side portions of the closure member squeezing together about the bracket body (see arrows 429 in FIG. 33), and frictional engagement between the locking ears and the sides of the bracket body yieldably resist any forces tending to reopen the closure member. Ideally, this breakover position or angle coincides with the pivot angle at which the shape of the central portion of the closure member transitions to exerting a neutral-to-negative camming force on the archwire.

With the form of bracket body 412 and closure member 422 described above, having the camming surfaces of the closure member positioned along opposite sides of the bracket body, it is preferable to use a different form of bumper 440. In this embodiment, rather than having a bumper 340 with leaf spring-type members disposed within the archwire slot, the bumper 440, also describable as a rotation spring, includes a pair of tabs 450, positioned on each side of the bracket body, laterally adjacent opposite ends of the archwire slot 414, to resiliently bias the archwire against opposing side portions of the closure member 422. This overall structure increases the width of the bracket/closure member engagement of the archwire and provides better torsional control of the tooth.

Figure 30:
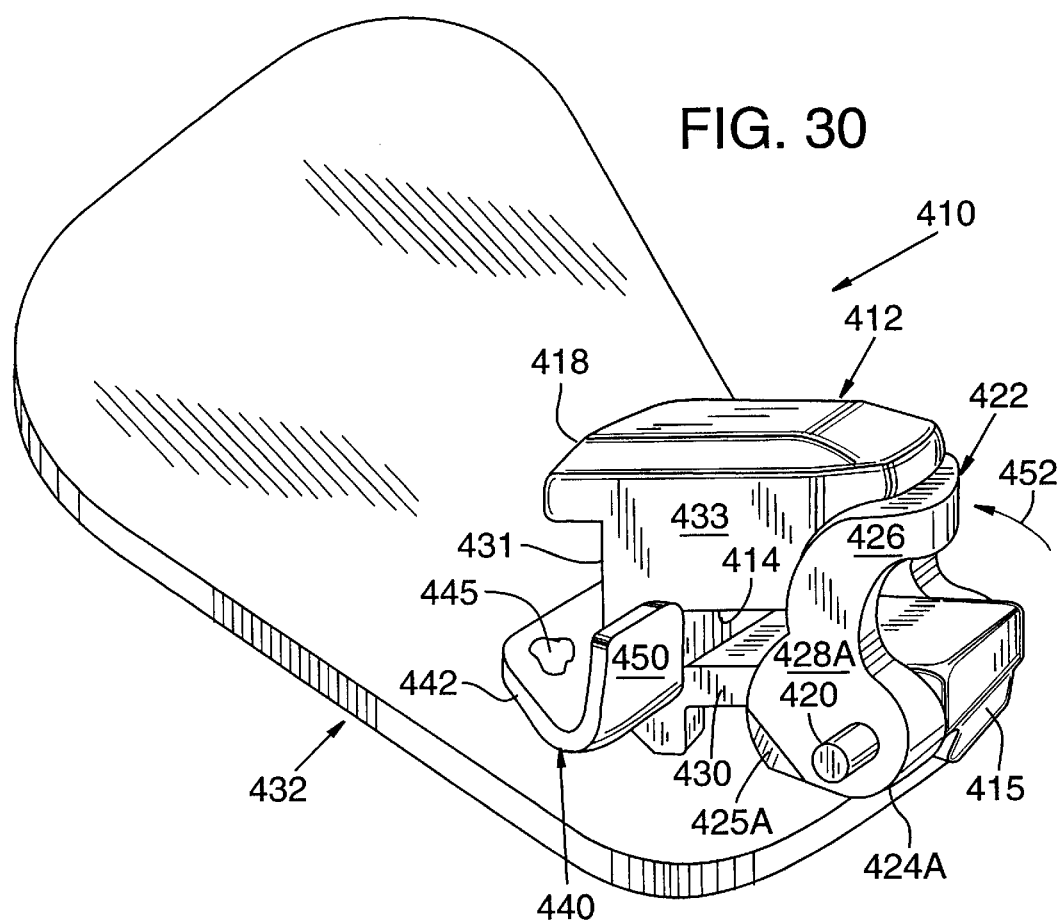
FIG. 30 is a perspective view of an improved, presently preferred, embodiment of the invention.

In general, the bumper 440 is a U-shaped spring member having a central portion 442 extending around the backside 431 of the bracket body 412 and supporting the end tabs 450 alongside the archwire slot 414. The end tabs actually protrude into a lateral extension of an archwire space alongside the archwire slot on each side of the bracket, where the tabs 450 will engage the archwire 16 on opposite sides of the bracket body. As shown in FIGS. 30 and 33, the bumper spring 440 is preferably affixed to the bonding pad 432 by means of a weld or brazing 445. As shown in FIG. 33, the bumper pad is formed in two layers: a first layer 440A, which engages the archwire 16, and a reinforcing layer or portion 440B. The reinforcing portion could alternatively be formed by ridges embossed into a single layer of sheet spring metal. The position of reinforcing layer 440B in FIG. 32, toward or away from the archwire slot, controls or adds the extent of spring force applied to the archwire.

If desired, a hook 421 can be incorporated into the hinge pin 420.

Having described and illustrated the principles of the invention in several embodiments thereof, it should be apparent that the invention can be modified in arrangement and detail without departing from such principles. For example, the arrangement of the archwire slot and closure member can be varied for different sizes and shapes of archwires, the bases of the brackets can be differently angled or of varying thicknesses, or the shapes of the tie wings can be varied. I claim all modifications and variation coming within the spirit and scope of the following claims.

I claim:

1. An improved lingual orthodontic bracket comprising:
    a bracket body having a three-sided archwire slot for receiving an archwire and a hinge formed on a side of the archwire slot;
    a closure member pivotally connected to the hinge to rotate across the archwire slot;
    the closure member including a first distal end connected pivotally by the hinge to the bracket body, a second distal end, and a central portion shaped to extend across the archwire slot when pivoted to a closed position to retain the archwire seated in shear in the archwire slot;
    the central portion of the closure member being formed with a first surface portion that faces the archwire slot and has a convex shape that exerts a positive camming force on the archwire to seat it in the slot as the closure member is rotated toward the closed position; and
    a bumper positioned adjacent a bottom wall of the archwire slot so as to cushion the archwire when pressed into the archwire slot by the closure member.

2. A lingual bracket according to claim 1 in which the bracket body and a closure member include means for interengaging the closure member and bracket body to retain the closure member in the closed position.

3. A lingual bracket according to claim 1 in which the bumper is mounted within the archwire slot.

4. A lingual bracket according to claim 1 in which the bumper includes a spring member mounted adjacent an end of the archwire slot.

5. A lingual bracket according to claim 1 in which the bumper includes a leaf-spring member extending lengthwise along the archwire slot to resiliently bias the archwire against the closure member.

6. A lingual bracket according to claim 5 in which the bumper is formed as a generally T-shaped member having a stem portion having a first end connected to a bonding pad supporting the bracket body and a cross-bar portion connected to a second end of the stem portion to form the leaf-spring member.

7. A lingual bracket according to claim 1 in which the bumper includes a U-shaped spring member extending around the bracket body and having a pair of end tabs, the end tabs positioned on each side of the bracket body laterally adjacent opposite ends of the archwire slot to resiliently bias the archwire against the closure member.

8. A lingual bracket according to claim 7 in which the U-shaped member has a central portion supporting the end tabs, the central portion extending around a portion of the bracket body and the end tabs bent to protrude into a lateral extension of the archwire slot.

9. A lingual bracket according to claim 8 in which the central portion of the U-shaped member is connected to a bonding pad supporting the bracket body.

10. A lingual bracket according to claim 7 in which the bumper includes a reinforcing portion positioned to add a spring component to the end tabs against the archwire.

11. An improved lingual orthodontic bracket comprising:
    a bracket body having a three-sided archwire slot for receiving an archwire and a hinge formed on a side of the archwire slot;
    a closure member pivotally connected to the hinge to rotate across the archwire slot;
    the closure member including a first distal end connected pivotally by the hinge to the bracket body, a second distal end, and a central portion shaped to extend across the archwire slot when pivoted to a closed position to retain the archwire seated in shear in the archwire slot;
    the central portion of the closure member being formed with a first surface portion that faces the archwire slot and has a convex shape that exerts a positive camming force on the archwire to seat it in the slot as the closure member is rotated toward the closed position; and
    the central portion of the closure member being formed in first and second side portions spaced laterally apart to straddle the bracket body.

12. A lingual bracket according to claim 11 in which each side portion includes one of said first distal ends pivotally connected by the hinge to the bracket body on opposite sides thereof and one of said central portions positioned to extend across the archwire slot on opposite sides of the bracket body.

13. A lingual bracket according to claim 12 in which the second distal end of the closure member is formed in a generally U-shape to interconnect the first and second side portions.

14. A lingual bracket according to claim 12 in which the bracket body includes a first tie wing on a side of the archwire slot opposite the hinge and the second distal end of the closure member is shaped to form a tie wing extending away from the bracket body.

15. A lingual bracket according to claim 11 in which each side portion of the closure member includes a locking portion protruding inward toward opposite sides of the bracket body, the bracket body having opposite side faces positioned to engage interferingly the locking ear portions of the closure member, such that, when the closure member is rotated into the closed position, the locking ear portions engage the side faces of the bracket body, thereby holding the closure member in the closed position.

16. A lingual bracket according to claim 15 in which the side faces of the bracket body are each positioned along a base portion of the bracket below the archwire slot and the locking ear portions are positioned between the first surface portion and the first distal end of the closure member.

17. A lingual bracket according to claim 15 in which the locking ear portions and side faces are mutually positioned and arranged to interengage through a limited angle coinciding with the exertion of said positive camming force.

18. A lingual bracket according to claim 17 in which the side faces of the bracket body are relieved to form a shoulder to receive the locking ear portion when the closure member is fully closed.

19. A lingual bracket according to claim 17 in which the central portion of the closure member is formed with a second surface portion having a shape that exerts a neutral to negative camming force on the archwire to retain it seated in the slot once the closure member is rotated into the closed position.

20. A lingual bracket according to claim 11 in which the central portion of the closure member is formed with a second surface portion having a shape that exerts a neutral to negative camming force on the archwire to retain it seated in the slot once the closure member is rotated into the closed position.

21. A lingual bracket according to claim 11 in which the hinge includes a pin having a laterally protruding hook on an end thereof.

22. A lingual bracket according to claim 11 including a bumper positioned adjacent a bottom wall of the archwire slot so as to bias the archwire resiliently against the closure member.

23. A lingual bracket according to claim 22 in which the bumper includes a U-shaped spring member extending around the bracket body and having a pair of end tabs, the end tabs positioned on each side of the bracket body laterally adjacent opposite ends of the archwire slot to resiliently bias the archwire against the closure member.

24. A lingual bracket according to claim 22 in which the U-shaped member has a central portion supporting the end tabs, the central portion extending around a portion of the bracket body and the end tabs bent to protrude into a lateral extension of the archwire slot.

25. A lingual bracket according to claim 22 in which the central portion of the U-shaped member is connected to a bonding pad supporting the bracket body.

26. A lingual bracket according to claim 22 in which the bumper includes a reinforcing portion positioned to add a spring component to the end tabs against the archwire.

* * * * *